(12) United States Patent
Dunshee

(10) Patent No.: US 7,267,681 B2
(45) Date of Patent: *Sep. 11, 2007

(54) WOUND CLOSURE SYSTEM AND METHOD

(75) Inventor: Wayne K. Dunshee, Maplewood, MN (US)

(73) Assignee: 3M Innovative Properties Company, St. Paul, MN (US)

(*) Notice: Subject to any disclaimer, the term of this patent is extended or adjusted under 35 U.S.C. 154(b) by 141 days.

This patent is subject to a terminal disclaimer.

(21) Appl. No.: 11/159,010

(22) Filed: Jun. 22, 2005

(65) Prior Publication Data

US 2005/0240221 A1 Oct. 27, 2005

Related U.S. Application Data

(63) Continuation of application No. 10/154,576, filed on May 24, 2002, now Pat. No. 6,942,683.

(51) Int. Cl.
*A61B 17/08* (2006.01)
*A61F 13/00* (2006.01)

(52) U.S. Cl. .................. 606/214; 606/213; 602/54

(58) Field of Classification Search .......... 602/41–59; 606/213–216; 128/888, 889
See application file for complete search history.

(56) References Cited

U.S. PATENT DOCUMENTS

| RE24,906 E | 12/1960 | Ulrich |
| 3,568,675 A | 3/1971 | Harvey ................ 128/275 |
| 3,665,918 A | 5/1972 | Lindquist et al. ........... 128/156 |
| 3,677,250 A | 7/1972 | Thomas .................. 128/348 |
| 3,824,998 A | 7/1974 | Snyder .................... 128/157 |
| 4,141,363 A | 2/1979 | James et al. ............. 128/335 |
| 4,302,500 A | 11/1981 | Flora ..................... 428/284 |
| 4,472,480 A | 9/1984 | Olson |
| 4,605,005 A | 8/1986 | Sheehan ................. 128/335 |
| 4,612,230 A | 9/1986 | Liland et al. ............ 428/167 |
| 4,702,251 A | 10/1987 | Sheehan ................. 128/335 |
| 4,726,989 A | 2/1988 | Mrozinski |
| 4,780,168 A | 10/1988 | Beisang et al. ........... 156/256 |

(Continued)

FOREIGN PATENT DOCUMENTS

EP 0 676 183 A1 10/1995

(Continued)

OTHER PUBLICATIONS

Collins et al., *Experiments in Polymer Science* 1973; Wiley, New York: Title page, Publication page, Table of Contents, and pp. 146-153.

(Continued)

*Primary Examiner*—Kim M. Lewis
(74) *Attorney, Agent, or Firm*—Nancy M. Lambert

(57) ABSTRACT

Methods and systems for closing wounds using wound closures and a flowable adhesive skin paint are disclosed. The flowable adhesive does not adhere the wound closures to the skin over the wound to reduce irritation. In some embodiments, the skin paint may include 1-40% of a siloxane-containing polymer; 60-99% of an Alkane-Based Siloxane Polymer Reaction Solvent; and 0-15% of adjuvants. The wound closures used with such a skin paint may include a wound bridging portion of microporous polypropylene film.

10 Claims, 4 Drawing Sheets

U.S. PATENT DOCUMENTS

| | | | |
|---|---|---|---|
| 4,815,468 A | 3/1989 | Annand | 128/335 |
| 4,825,866 A | 5/1989 | Pierce | 128/335 |
| 4,950,282 A | 8/1990 | Beisang et al. | 606/216 |
| 4,995,114 A | 2/1991 | Price, Jr. | 2/15 |
| 5,176,703 A | 1/1993 | Peterson | 606/216 |
| 5,230,701 A | 7/1993 | Meyer et al. | |
| 5,254,132 A | 10/1993 | Barley et al. | |
| 5,259,835 A | 11/1993 | Clark et al. | |
| 5,377,695 A | 1/1995 | An Haack | 128/888 |
| 5,445,597 A | 8/1995 | Clark et al. | |
| 5,480,935 A | 1/1996 | Greff et al. | |
| 5,497,788 A | 3/1996 | Inman et al. | 128/888 |
| D371,604 S | 7/1996 | Savage et al. | D24/145 |
| 5,531,855 A | 7/1996 | Heinecke et al. | 156/252 |
| 5,534,010 A | 7/1996 | Peterson | 606/215 |
| 5,538,500 A | 7/1996 | Peterson | 602/48 |
| 5,630,430 A | 5/1997 | Shultz et al. | 128/888 |
| D385,038 S | 10/1997 | Shultz | D24/189 |
| 5,753,699 A | 5/1998 | Greff et al. | |
| 6,107,219 A | 8/2000 | Joseph et al. | |
| 6,214,332 B1 | 4/2001 | Askill et al. | |
| 6,383,502 B1 | 5/2002 | Dunshee et al. | |
| 6,942,683 B2 * | 9/2005 | Dunshee | 606/214 |
| 2001/0037077 A1 | 11/2001 | Wiemken | 602/41 |

FOREIGN PATENT DOCUMENTS

| | | |
|---|---|---|
| GB | 831401 | 3/1960 |
| GB | 2 251 796 A | 7/1992 |
| WO | WO92/10983 | 7/1992 |
| WO | WO93/17633 | 9/1993 |
| WO | WO98/26719 | 6/1998 |
| WO | WO 00/06213 A1 | 2/2000 |
| WO | WO 00/49983 | 8/2000 |
| WO | WO 00/56280 A1 | 9/2000 |
| WO | WO 02/26181 | 4/2002 |

OTHER PUBLICATIONS

Van Nostrand-Reinhold, *Handbook of Pressure Sensitive Adhesive Technology*, Chapter 18, 1983; Van Nostrand Reinhold Company, New York: Title page, Publication page, Table of Contents and pp. 384-403.

Johnson and Johnson® Brand Butterfly Closures, Sterile waterproof closures for small wounds and incisions, Medium closures 1¾×⅜ in. (4.5cm×1cm), Johnson and Johnson Consumer Products Company, Skillman, NJ, 2 pgs.(1995).

Product Sheet for BAND-AID Brand Adhesive Bandages from Johnson & Johnson Gateway LLC (3pgs.) from online retrieved Feb. 27, 2001.

Brochure entitled "3M™ Steri-Strip™ Elastic Skin Closures—Conformable closure even in the toughest places." 3M Health Care; 1997; No. 70-2008-6225-1(77.5)ii (1 sheet double-sided).

Brochure entitled "3M™ Steri-Strip™ Adhesive Skin Closures—Quality plus versatility . . . Because one size does not fit all"; 3M Innovation; 3M Health Care; 1994; No. 70-2008-8510-4(60.5)ii; (9 pgs.).

* cited by examiner

WOUND CLOSURE SYSTEM AND METHOD

CROSS REFERENCE TO RELATED APPLICATIONS

This application is a continuation of U.S. Ser. No. 10/154,576, filed May 24, 2002, now U.S. Pat. No 6,942,683, the disclosure of which is herein incorporated by reference.

TECHNICAL FIELD

The invention relates generally to the treating and closing of wounds using adhesive wound closures and adhesive skin paints.

BACKGROUND

In medicine, sutures have long been used to close wounds. More recently, adhesive closures have been introduced that can effectively close some types of wounds without inflicting the additional injury inherent in suturing. These adhesive closures have a backing to provide solid structure, and have an adhesive layer for adhering to the skin. There are two main criteria that must be reconciled in a successful design for these products: reliable adhesion to the skin, even when the wound is adjacent to a joint; and good performance in keeping the wound edges in proximity to each other.

One approach is to use a non-woven web as the basic backing, and to reinforce this material with strong fibers in the longitudinal, or cross-wound, direction. The main substance of the backing can bend with the skin as the patient moves, and the reinforcing fibers strengthen the lightweight backing so that the structure can resist wound edge separation. This backing is combined with a strong skin adhesive over the entire skin contacting surface. The strength of the reinforcing fibers, combined with their secure anchorage immediately adjacent to the wound edges provides excellent security against wound separation. For example, STERI-STRIPS wound closures, commercially available from Minnesota Mining and Manufacturing Company of St. Paul, Minn., are constructed in this way.

More recently, an improvement has been developed providing a wound closure including a wound bridging portion that has sufficient dimensional stability to hold the wound edges in proper alignment, even in the face of substantial stretching of the wound closure as a whole. The wound bridging portion is dimensionally stable where it is most needed, i.e., directly over the wound. The remainder of the wound closure is preferably substantially more extensible and elastic than the wound bridging portion to improve conformability and adhesion of the wound closure to the patient. More specifically, the wound closure has an adhesive for adhering the wound closure to skin, opposing elastomeric end portions, and a wound bridging portion between the end portions. The wound closure is constructed such that it recovers at least 85% after being stretched 30%, and such that the wound bridging portion stretches less than the end portions when subjected to the same force. In this way, the wound bridging portion tends to maintain the wound closed against forces generated by stretching of skin. Such a wound closure is disclosed in copending U.S. patent application Ser. No. 09/671,129 filed Sep. 27, 2000 and entitled CONFORMABLE ADHESIVE WOUND CLOSURES.

A different strategy for achieving adhesion to the skin and resistance to forces tending to open the wound edges is disclosed in U.S. Pat. No. 5,259,835 (Clark et al.). In that reference, a wound closure is provided employing a porous bonding member which receives a flowable adhesive capable of providing long-term wound support. In particular, cyanoacrylates are mentioned as being suitable for the flowable adhesive. A disadvantage of that system is that once the porous bonding member has received the flowable adhesive, and the adhesive has bonded to the skin, it becomes a rigid unit which can cause skin irritation along its edges as body movement flexes the skin against those edges.

Another group of adhesives which have utility for skin contacting application is disclosed in U.S. Pat. No. 6,383,502 (Dunshee et al.). These substances have good skin compatibility, and are hydrophobic so that they tend not to remain in the interior of wounds. However, their tensile strength is only sufficient for, e.g. closing or sealing skin cracks, not for holding major wounds closed against the range of motion skin is normally subjected to.

SUMMARY OF THE INVENTION

The present invention addresses the problems discussed above by providing a system for closing wounds that employs both wound closures and a flowable adhesive skin paint for providing good wound edge opposition in the spaces adjacent to or between the wound closures. The combination of a wound closure that can hold the wound edges closed in the face of substantial forces trying to separate them, and a flowable adhesive that can hold wound edges in excellent opposition but cannot sustain large forces, accomplish much more together than either alone. Unlike previously known systems employing both a wound closure and a flowable adhesive, the skin paint is adhesive to skin but not to the wound closure, and thus mechanical irritation of the skin near the wound is avoided.

As used in connection with the present invention, "flowable adhesive skin paint" means a liquid polymeric coating composition that may be cured and/or dried to leave a flexible coating adhered to the skin, nails and mucous membranes The liquid compositions can be cured and/or dried at room temperature (20.degree. C.) when applied to skin, nails, or mucous membranes of a user. By "flexible" it is meant that the coating does not crack in response to ordinary skin flexion. The liquid composition and/or dried polymer film can have various medicaments or other agents incorporated therein for maintaining sterility and/or for release to the underlying area of the body of a user. For example, perfumes, antimicrobial, botanicals, medicaments, or similar materials can be released from the coatings.

In one aspect, the present invention provides a method of tending a wound by retaining opposing edges of a wound together by adhering one or more wound closures to skin on opposing sides of the wound, each wound closure of the one or more wound closures including a backing, a layer of adhesive on one major surface of the backing, and a wound bridging portion, wherein the wound bridging portion of each wound closure of the one or more wound closures contacts the opposing edges of the wound. In this aspect, the method further includes applying flowable adhesive skin paint to the wound adjacent the one or more wound closures after adhering the one or more wound closures across the wound using the layer of adhesive on the one or more wound closures; wherein the adhesive skin paint does not adhere the one or more wound closures to the skin over the wound.

In another aspect, the present invention provides a method of tending a wound by retaining opposing edges of a wound together by adhering one or more wound closures to skin on opposing sides of the wound, each wound closure of the one or more wound closures including a backing, a layer of adhesive on one major surface of the backing, and a wound bridging portion, wherein the wound bridging portion of each wound closure of the one or more wound closures contacts the opposing edges of the wound, and wherein the wound bridging portion of each wound closure of the one or more wound closures in contact with the opposing edges of the wound includes a microporous polypropylene film. In this aspect, the method further includes applying flowable adhesive skin paint to the wound adjacent the one or more wound closures after adhering the one or more wound closures across the wound using the layer of adhesive on the one or more wound closures, wherein the adhesive skin paint includes 1-40% of a siloxane-containing polymer; 60-99% of an Alkane-Based Siloxane Polymer Reaction Solvent; and 0-15% of adjuvants; wherein adhesion strength between each wound bridging portion in contact with the opposing edges of the wound and skin is about 30 grams/centimeter or less.

In another aspect, the present invention provides a wound closure system including a quantity of a flowable adhesive skin paint; and at least one wound closure that includes a backing, a wound bridging portion adapted to be placed over a wound, and a pressure sensitive adhesive, wherein the adhesive skin paint does not adhere the wound bridging portion of the at least one wound closure to skin.

In another aspect, the present invention provides a wound closure system including a quantity of a flowable adhesive skin paint comprising 1-40% of a siloxane-containing polymer; 60-99% of an Alkane-Based Siloxane Polymer Reaction Solvent; and 0-15% of adjuvants; and at least one wound closure that includes a backing, a wound bridging portion including a microporous polypropylene film adapted to be placed over a wound, and a pressure sensitive adhesive, wherein adhesion strength between the wound bridging portion and skin is about 30 grams/centimeter or less.

The adhesive skin paint may be of a type that is non-stinging when applied to the skin. One group of suitable skin paints which have this property included those described in U.S. Pat. No. 6,383,502 (Dunshee et al.), discussed briefly above. One manner of characterizing these compositions is adhesive skin paints comprising a) 1-40% of a siloxane-containing polymer; b) 60-99% of an Alkane-Based Siloxane Polymer Reaction Solvent; and c) 0-15% of adjuvants.

It may be preferred that the adhesive skin paint used in connection with the present invention not substantially adhere the wound bridging portion of the wound closure to the skin. As used in connection with the present invention, the term "not adhere" may be quantified as, for example, providing an adhesive force of about 80 grams/inch (about 30 grams/centimeter) or less; in some instances about 50 grams/inch (about 20 grams/centimeter) or less.

When adhesive skin paints of the type described in U.S. Pat. No. 6,383,502 are in use, the limited adhesion between the wound bridging portion and skin as caused by the adhesive skin paint may be accomplished by fabricating the wound bridging portion from a porous film, e.g., a porous polypropylene film. The porous nature of the film may provide advantages such as allowing the wound to breathe and allowing the solvent portion of any adhesive skin paint that has inadvertently been permitted under the wound bridging portion to evaporate. The porous film may be microporous, where microporous films have pore sizes of about 100 micrometers or less. One example of a suitable microporous film may be a microporous polypropylene film.

The wound closures used in connection with the present invention may preferably have a backing made from an elastomeric web, preferably a nonwoven elastomeric web including thermoplastic elastomeric melt blown fibers. The backing material preferably has multi-directional elastic properties, so much so that the wound closure recovers at least 85% after being stretched 30% or less. More preferably, the backing recovers at least 95% after being stretched 30% or less.

When discussing recovery and stretching in terms of percentages, it should be understood that percent recovery means that after an appropriate period of time, e.g., 1 minute or less, the wound closure or the relevant portion of the wound closure recovers that percentage of its increased length. For example if a wound closure was stretched by 1 centimeter over its original length, an 85% recovery would mean that after stretching (i.e., when the stretching forces are removed) the wound closure shrinks by 0.85 centimeters. Stretching percentages are defined in a similar manner. For example, if a wound closure having an unstretched length of 1 centimeter is stretched 30%, its length after stretching (but before recovery) would be 1.3 centimeters.

The wound bridging portion is preferably relatively dimensionally stable as compared to the remainder of the backing, i.e., the wound bridging portion stretches less than the remainder of the wound closure, e.g., the opposing end portions, when the wound closure is subjected to a stretching force. The wound bridging portion preferably stretches 8% or less when the wound closure stretches 30% or less. More preferably, the wound bridging portion stretches 5% or less when the wound closure stretches 30% or less, and most preferably the wound bridging portion stretches 1% or less when the wound closure stretches 30% or less. In some instances, the wound bridging portion may experience some elongation, i.e., stretches more than 0%, when the wound closure is stretched.

A reinforcing layer that is separate from a backing may be used in the wound bridging portion of the wound closure to provide the desired dimensional stability to the wound bridging portion. That reinforcing layer may take the form of a wound contact layer (i.e., a layer in contact with a wound when in use) if it is located on the patient side of the wound closure. Alternatively, for example, the reinforcing layer may be located on the side of the backing facing away from the wound. In still another alternative, a reinforcing layer may be provided on both sides of the backing in the wound bridging portion.

Regardless of its location, it is preferred that the reinforcing layer be firmly attached to the backing such that the reinforcing layer does not delaminate from the wound closure when the wound closure stretches, more preferably, the reinforcing layer does not delaminate from the wound closure when the wound closure stretches 30%. The reinforcing layer may be attached to the wound closure using any suitable technique, e.g., adhesives, welding, etc.

The wound closures of the invention also include adhesive for attaching the wound closure to the skin. The adhesive is preferably a pressure sensitive adhesive. Preferably, this is a relatively aggressive adhesive, capable of taking a firm grip on the patient's skin to prevent unwanted detachment. The adhesive used to attach the wound closure to the patient's skin may also be used to attach a reinforcing layer to the wound closure in the wound bridging portion if that adhesive is strong enough to prevent delamination of the reinforcing layer from the wound closure when the wound closure stretches.

In some embodiments, the wound bridging portion may have a width less than a width of the end portions. This permits maximum visualization of the wound area without sacrificing the surface area where the skin adhesive contacts the patient's skin. It may also be convenient to have the opposing end portions have unequal lengths as measured from the wound bridging portion to the ends of the wound closure. This sometimes facilitates placing the wound closure when features such as the eye are near the wound site.

These and other features and advantages of the present invention are discussed in connection with illustrative embodiments of the invention below.

BRIEF DESCRIPTION OF THE DRAWING

In the several figures of the attached drawing, like parts bear like reference numerals, and.

DETAILED DESCRIPTION OF ILLUSTRATIVE EMBODIMENTS OF THE INVENTION

Figure 1:
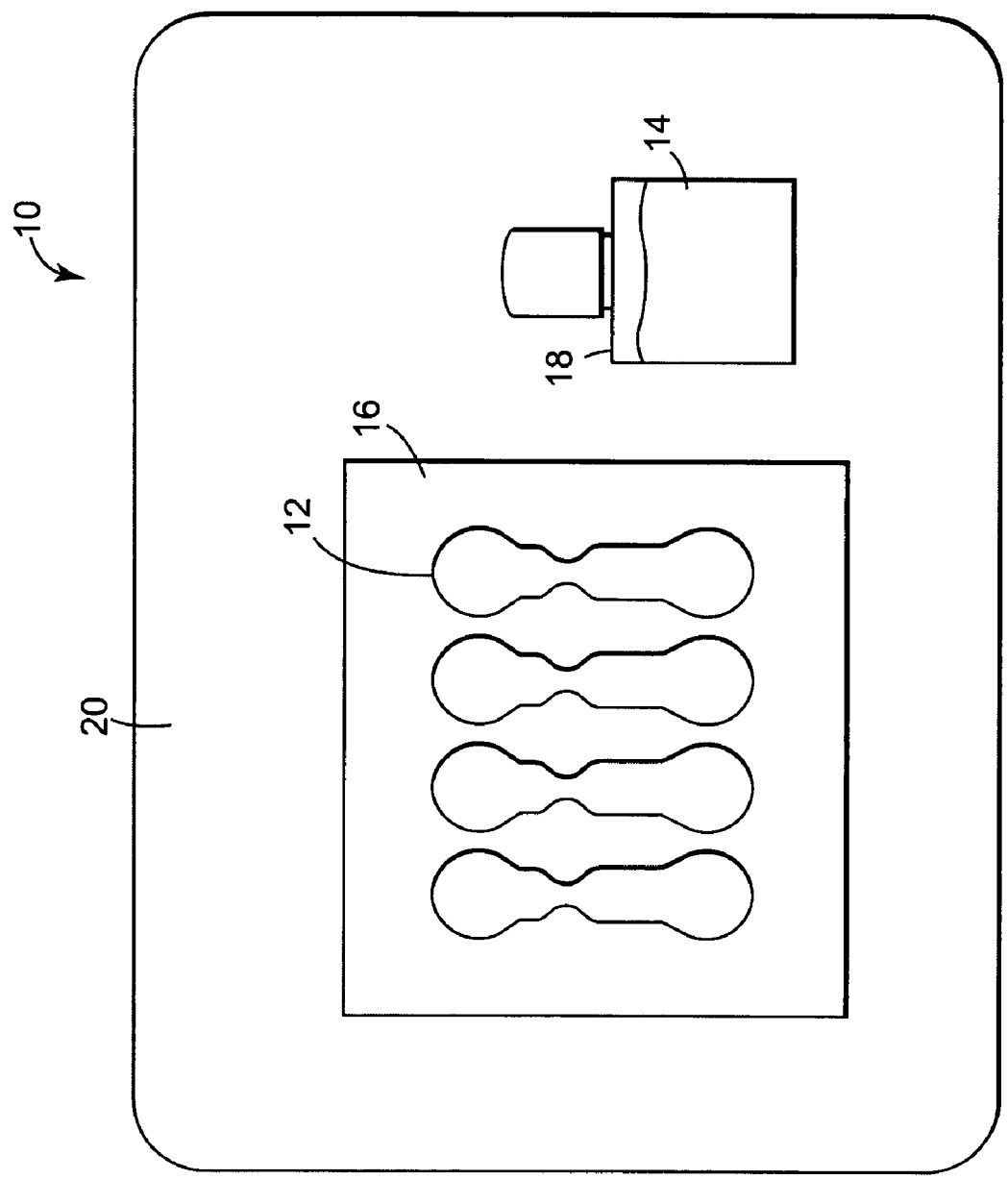
FIG. 1 illustrates a plan view on a kit embodying a skin closure system according to the present invention.

Referring now to FIG. 1, an exemplary wound closure system 10 is illustrated in the form of a kit. The kit 10 includes wound closures 12 and a quantity of adhesive skin paint 14. The wound closures 12 may be mounted on a release liner 16, while the adhesive skin paint 14 may be provided in a dispensing bottle 18 or other container. The system 10 may preferably be provided in a package 20. In some embodiments, the package 20 may be adapted to cooperate with some method for sterilizing the kit, e.g. the package may include a layer of a spun bonded polyolefin (such as TYVEK) which is permeable to ethylene oxide gas.

Figure 2:
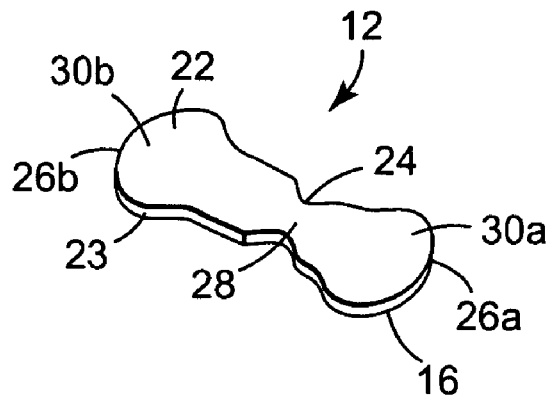
FIG. 2 illustrates a perspective view of a wound closure made according to the present invention.
Figure 3:
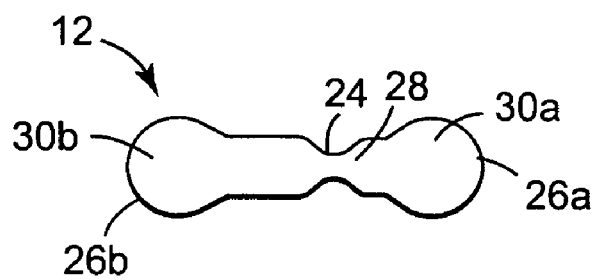
FIG. 3 illustrates a top plan view of the wound closure in FIG. 2.

Referring now to FIGS. 2 and 3, an exemplary wound closure 12 is illustrated in isolation. The wound closure 12 has a backing 22 and a layer of skin adhesive 23 contacting the backing. In the embodiment depicted in these figures, the release liner 16 is shown diecut to size rather than cut to support several wound closures as in FIG. 1. In either case the release liner 16 serves to protect the adhesive layer 23 between the time the wound closure 12 is made and the time when it is to be applied to the skin.

The wound closure 12 includes a wound bridging portion 24 located between opposing end portions 26a and 26b. The wound bridging portion 24 preferably includes a neck 28 where the width narrows as compared to the opposing end portions 26a and 26b (where width is measured transverse to the length of the wound closure 12). The neck 28 of the wound bridging portion 24 is intended to be placed directly over the wound edges on the body so that the maximum practical amount of the wound can be seen by medical practitioners.

Pad portions 30a and 30b are preferably located at the distal ends of the end portions 26a and 26b of the wound closure 12. The pad portions 30a and 30b may widen as illustrated to increase the surface area available for the adhesive layer 24 to take an adhesive purchase on the skin.

Referring to FIG. 3, it may be preferred that the wound closure 12 is not symmetrical from end to end, but rather the lengths of the opposing end portions 26a and 26b as measured from the wound bridging portion 24 are unequal, i.e., one of the end portions 26a is shorter than end portion 26a and 26b. The benefits of such an asymmetrical arrangement were discussed in greater detail above.

Figure 4:
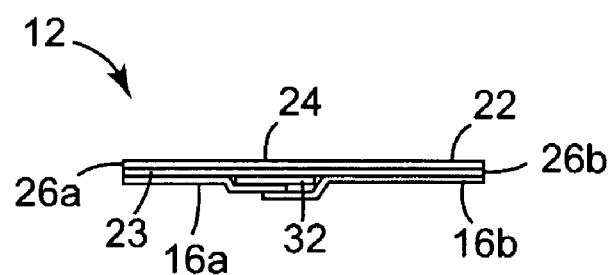
FIG. 4 illustrates a side view of the wound closure of FIG. 3.

A side view of the wound closure of FIG. 3 is depicted in FIG. 4. In this view it may be seen that the release liner 16 may conveniently be divided into two slightly overlapping sections 16a and 16b. This arrangement facilitates the peeling of the release liner 16 from the adhesive layer 23 immediately before use.

FIG. 4 also depicts a reinforcing layer 32 that may preferably be adhered to the adhesive layer 24. It may be preferred that the reinforcing layer 32 be attached to the wound closure 12 only in the wound bridging portion 24, more preferably the neck 28, in which case the end portions 26a and 26b are free of the reinforcing layer 32. It may be preferred that the reinforcing layer 32 be firmly attached to the wound closure 12 such that the reinforcing layer 32 does not delaminate from the wound closure 12 when the wound closure stretches. More preferably, the reinforcing layer 32 does not delaminate from the wound closure 12 when the wound closure stretches 30% or less. In the depicted embodiment, the reinforcing layer 32 is attached to the wound closure using the adhesive 23, although the reinforcing layer 32 may be attached to the wound closure 12 using any suitable technique, e.g., adhesive (the same or different than the adhesive used to attach the wound closure 12 to a patient), welding, etc.

If the reinforcing layer 32 is located on the same side of the wound closure 12 as the adhesive 23, then the materials used in the reinforcing layer 32 must be compatible with contact against wounded skin in addition to the desired elongation and elasticity characteristics. One advantage of positioning the reinforcing layer 32 on the same side of the wound closure 12 as the adhesive 23 is that the adhesive 23 in the wound bridging portion 24 may be covered by the reinforcing layer 32. Covering the adhesive 23 in that area may prevent the adhesive 23 from adhering to the wound edges and potentially causing problems when the wound closure 12 is removed.

As discussed above, it may also be desirable that the reinforcing layer 32 be porous. One suitable film which meets these several criteria is commercially available from 3M Co. of St. Paul, Minn. as PROPORE KN 9400 porous polypropylene film. Additional details regarding the preparation of the suitable film for the wound bridging portion can be found in U.S. Pat. No. 4,726,989 (Mrozinski). In any case, it may be preferred that the material of the reinforcing layer 32 have a thickness of about 75 micrometers (0.003 inch) or less. Thicker films may be more likely felt by the patient when placed against the tender wound edges. It may be more preferred that the reinforcing layer 32 have a thickness of about 60 micrometers (0.0023 inch) or less.

Figure 5:
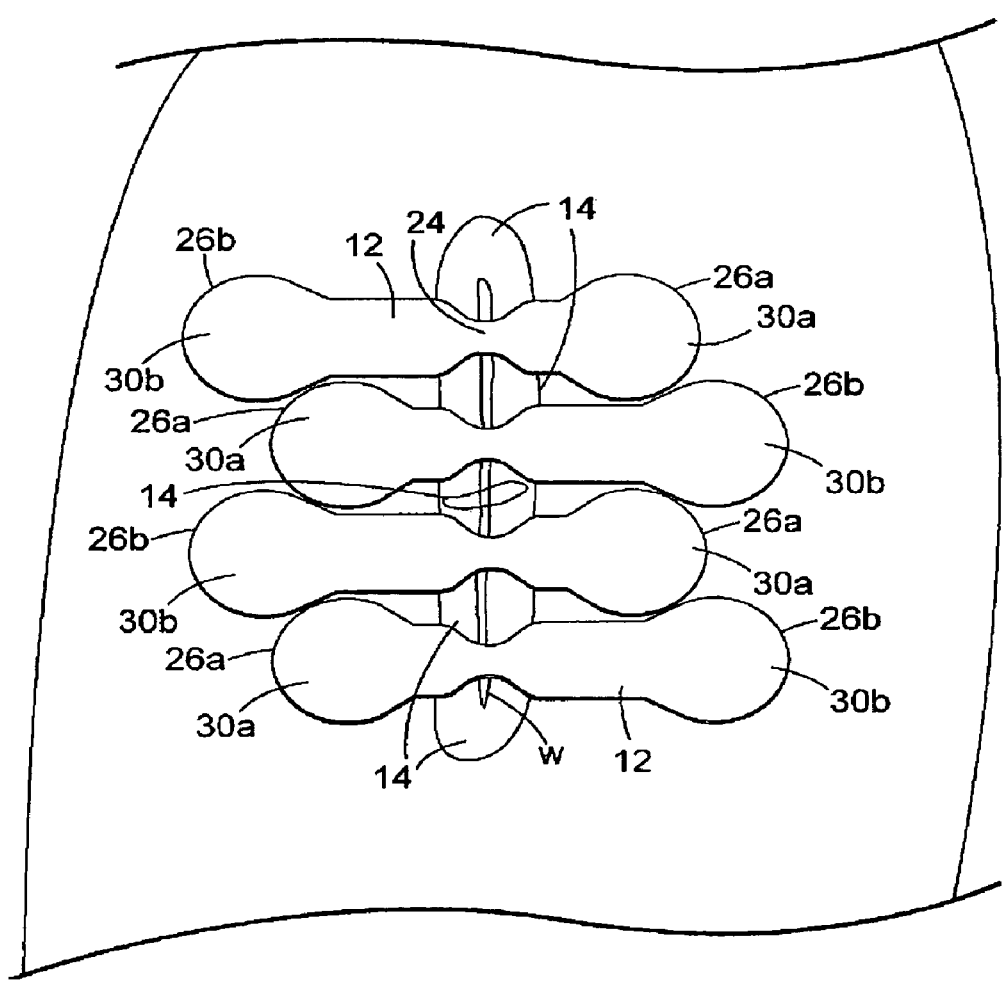
FIG. 5 illustrates four of the wound closures of the present invention used in coordination with an application of skin paint to hold the wound edges of a wound on the arm of a patient.

Referring now to FIG. 5, four wound closures 12 are used in coordination to hold together the wound edges of a wound (W), illustrated in this case on the arm of a patient. Of particular note is the alternating arrangement of the end portions 26a and 26b, with the long and short end portions 26a and 26b of the wound closures 12 being deployed on opposite sides of the wound alternately. The wider pad portions 30a and 30b may increase the holding power of the wound closures 12, but if the wound closures were end-for-end symmetrical, they might interfere with and overlap each other along a straight wound such as the one depicted. In other words, there would be a limit as to how closely they could be placed together, and that limit might preclude their use if the wound needed to be bound more densely. However, the figure illustrates how the unequal lengths of the end portions 26a and 26b allow the wound closures 12 to nest together for an excellent combination of reduced wound occlusion, sufficient points of binding across the wound per linear wound length, and increased surface area for taking a firm grip on the skin.

It will also be observed in FIG. 5 that regions of adhesive skin paint 14 have been laid down in areas adjacent to the wound closures 12. The regions where adhesive skin paint 14 have been applied are preferably adjacent to rather than under the wound closures 12. However, as depicted in FIG. 5, capillary action may sometimes draw the adhesive skin paint 14 under the bridging portion 24 of one or more of the wound closures 12. This issue may, however, be addressed if the wound closures 12 are porous within the wound bridging portion 24 so that any adhesive skin paint 14 drawn under the wound closure 12 may dry. In alternative methods, the adhesive skin paint 14 may be applied both over and adjacent to the adhesive wound closures 12. The porosity of the preferred adhesive wound closures 12 (at least within the wound bridging portion), however, allows for drying of any adhesive skin paint 14 between the adhesive wound closure 12 and the patient.

By porous or microporous (and variations thereof) as used herein when describing the wound bridging portion 24, it is meant that the wound bridging portion 24 is porous or microporous throughout its thickness, i.e., that all layers of materials (if two or more are present) located within the wound bridging portion are porous or microporous such that the skin paint beneath the wound bridging portion 24 could dry through the wound bridging portion (e.g., allow volatile components of the skin paint to pass through the wound bridging portion 24). For example, if the wound bridging portion 24 includes a layer of reinforcing material 32 and backing 22, both layers would be porous or microporous such that the skin paint beneath the wound bridging portion could dry through the wound bridging portion.

In addition to porosity, it is preferred that the wound bridging portion 24 is constructed such that the adhesive skin paint 14 does not adhere the bridging portion 24 of the wound closure 12 to the patient's skin. Alternatively, it may be sufficient that only those materials in contact with the patient may be constructed such that the adhesive skin paint 14 does not adhere the wound bridging portion of the wound closure 12 to the patient. It may further be preferred that all portions of the wound closure 12 in contact with the patient be constructed such that the adhesive skin paint 14 do not adhere the wound closure 12 to the patient.

Various elastomeric webs are suitable for use as backings 22 in wound closures 12 of the present invention; for example, thin layers of polyvinyl chloride foams may provide the desired properties. Certain nonwoven elastomeric webs based on melt blown webs of thermoplastic elastomeric small diameter fibers may, however, be preferred due to their exceptional conformability and moisture vapor transmission properties. More particularly, elastomeric thermoplastic materials from which microfiber webs can be prepared include, for example, elastomeric polyurethanes, elastomeric polyesters, elastomeric polyamides and elastomeric A-B-A' block copolymers wherein A and A' are styrenic moieties and B is an elastomeric midblock.

The elastomeric small diameter fibers preferred for use with the present invention may preferably have diameters of, e.g., from about 1 micrometer to greater than 50 micrometers, more preferably from about 5 micrometers to about 30 micrometers. The elastomeric web thus formed may preferably recover at least 85%, more preferably at least 90%, and most preferably at least 95%, in the machine direction after being stretched 30% or less. It may also be preferred that the web used for the backings 12 recover at least 80%, more preferably at least 85%, most preferably at least 90%, in the cross direction (i.e., transverse to the machine direction) after being stretched 30% or less in that direction.

Nonwoven melt blown elastomeric webs can be prepared by any suitable process. More information about some elastomeric webs suitable for use with the present invention can be found in U.S. Pat. No. 5,230,701 (Meyer et al.).

Suitable backings can also be formed from breathable nonwoven tape backings where the nonwoven tape backing includes a fibrous nonwoven web formed in part by multicomponent fibers having an adhesive component region. The multicomponent fibers are distributed throughout the width dimension of the nonwoven tape backing such that adhesive component region is exposed on both outer faces of the nonwoven tape backing. The adhesive component region is preferably a pressure-sensitive adhesive region formed by hot melt coextrusion of the adhesive component and at least one nonadhesive component to form the multicomponent fibers. The nonwoven tape backing is preferably formed simultaneously with the formation of the multicomponent fibers or simultaneously with the collection of the multicomponent fibers into the nonwoven backing. Details about how such materials can be formed and then provided with an adhesive layer may be found in U.S. Pat. No. 6,107,219 (Joseph et al.).

The backing 22 is preferably coated with a skin compatible pressure sensitive adhesive layer 23. When multicomponent fiber backings as described above are used for the backing, it may be particularly convenient to prepare a melt blown microfiber pressure sensitive adhesive web and then laminate this web to the backing. The examples entitled "Adhesive Sample" 1, 2, and 3 in U.S. Pat. No. 6,107,219 (Joseph et al.) disclose materials and methods that may be suitable for use with the present invention.

Other preferred pressure sensitive adhesives which can be used in the adhesive layer of the present invention are the normal adhesives which are applied to the skin such as the acrylate copolymers described in U.S. Pat. RE 24,906, particularly a 97:3 weight ratio iso-octyl acrylate:acrylamide copolymer or a 96:4 weight ratio iso-octyl acrylate:acrylamide copolymer. Other medical grade skin adhesives such as copolymers of iso-octyl acrylate and N-vinyl pyrrolidone, or copolymers of iso-octyl acrylate and acrylic acid, can also be used.

Liners which are suitable for use in connection with the wound closures of the present invention can be made of kraft papers, polyethylene, polypropylene, polyester or composites of any of these materials. The liners may preferably be coated with release agents such as fluorochemicals or silicones. For example, U.S. Pat. No. 4,472,480 (Olson) describes low surface energy perfluorochemical liners. Some preferred liners are papers, polyolefin films, or polyester films coated with silicone release materials. One example of a commercially available release liner that may be considered suitable for use with the present invention is a silicone coated release paper available as SC 50 1F M4D from Sopal France, of Dax, France. Also considered suitable is ESP-48 liner, commercially available from DCP-Lohja of Cullman, Ala.

Other combinations of adhesives and liners are contemplated for use with embodiments according to the present invention. Those skilled in the art will be familiar with the processes of testing a new adhesive against different liners or a new liner against different adhesives to arrive at the combination of qualities desired in a final product. The considerations pertinent to the selection of a silicone release liner can be found in Chapter 18 of the Handbook of Pressure Sensitive Adhesive Technology, Van Nostrand-Reinhold, 1982, pp. 384-403. U.S. Pat. No. 4,472,480 also describes considerations pertinent to the selection of a perfluoropolyether release liner.

The wound closures according to the present invention may be conveniently made by preparing the backing as a long, indefinite length web which is slit to widths appropriate to the closure to the made. The adhesive layer may then be applied by any suitable technique, e.g., curtain coating, knife coating, melt blowing, etc. Where desired, a narrow ribbon of material is laid down onto the adhesive layer to form the reinforcing layer. Typically, a release liner is laminated to this construction, either in a single layer or in an overlapped two-piece arrangement as desired. Wound closures are then die cut from the laminated construction, piercing the release liner if individual closures are desired, or sparing the release liner if an arrangement including a plurality of wound closures 12 on a release liner 16 according to FIG. 1 is desired. Conventional slitting and die cutting techniques will serve in a fashion well known to the artisan.

Figure 6:
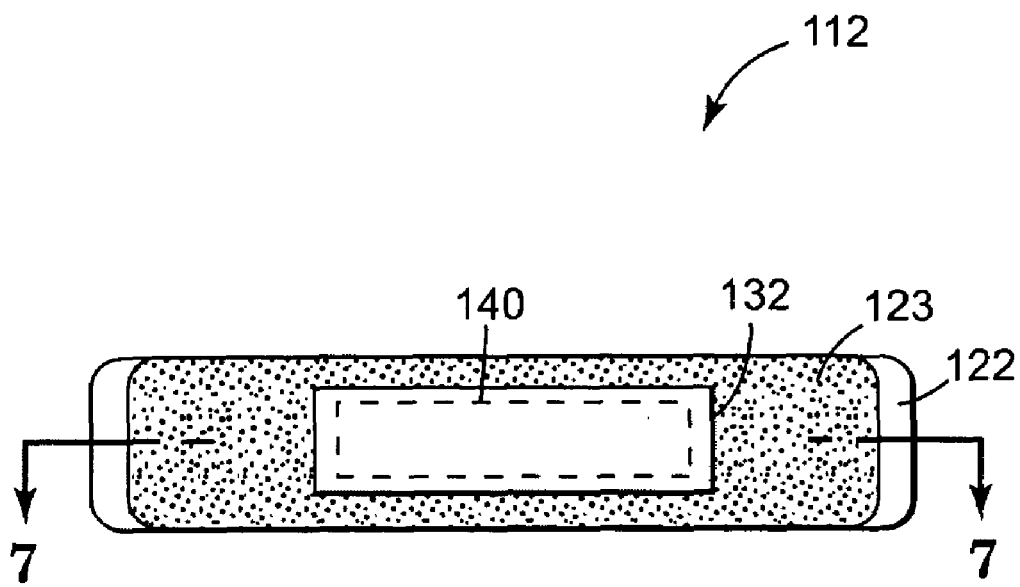
FIG. 6 depicts the patient side of an adhesive wound closure that may be used in connection with the systems and methods of the present invention.
Figure 7:
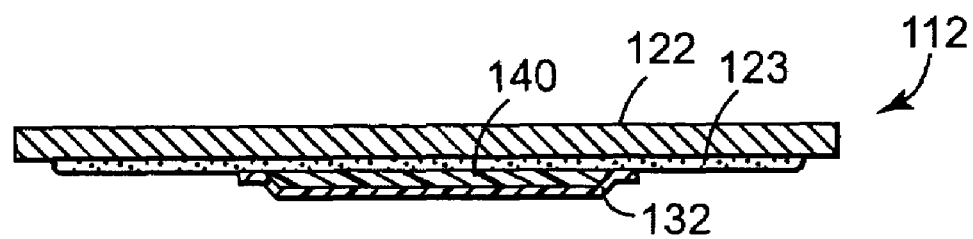
FIG. 7 is a cross-sectional view of the adhesive wound closure of FIG. 6, taken along line 7-7 in FIG. 6).

FIGS. 6 & 7 depict another wound closure 112 that includes a backing 122 with a skin adhesive 123 located thereon. The wound closure 112 also includes a reinforcing layer 132 that may define a wound bridging portion as described above. The wound bridging portion of wound closure 112 is not, however, narrowed or necked as in the embodiments described above.

An additional option component depicted in connection with wound closure 112 is an absorbent layer 140 that is located between the reinforcing layer 132 and the skin adhesive 123 (which is why the absorbent layer 140 is depicted in broken lines in FIG. 6. The exact location of the absorbent layer 140 in the wound closure 112 may, however, vary. For example, in some embodiments, the absorbent layer 140 may be located on the opposite side of the backing 122 from the reinforcing layer 132.

The absorbent layer 140 may be present to provide one or more functions in connection with wound closure 112. For example, the absorbent layer 140 may be present to absorb wound exudate. Another function that may be performed by the absorbent layer 140 is absorption of skin paint. For example, if an excess amount of skin paint is applied after the wound closure is in position across a wound, the absorbent layer 140 may absorb at least some of the excess skin paint, thereby preventing it from, e.g., entering the wound, pooling on the skin, etc. As a result, it may be preferred that the absorbent layer 140 exhibit an affinity for the skin paint used in connection with wound closures according to the present invention. Examples of suitable materials for the absorbent layer 140 include, e.g., but are not limited to: woven materials, nonwoven materials, foams, etc.

It may be that in some embodiments, the reinforcing layer itself may also exhibit some absorbent properties in addition to reinforcing the wound bridging portion.

Although the methods of the present invention may preferentially involve selective application of skin paint to a wound adjacent a single adhesive wound closure or between adjacent pairs of wound closures, incorporating absorbent materials in the construction of the wound closures may allow a user to more liberally apply the skin paint with the knowledge that any skin paint applied directly to the wound closure or seeping between the wound closure and the patient may be absorbed by an absorbent layer (in addition to not adhering the wound closure to the patient).

The methods and systems of the present invention may include an adhesive skin paint that includes cyanoacrylate-based adhesive compatible with wound care. Examples of such materials may be described in, e.g., U.S. Pat. No. 5,254,132 (Barley et al.); U.S. Pat. No. 5,480,935 (Greffet al.); U.S. Pat. No. 5,753,699 (Greff et al.); U.S. Pat. No. 6,214,332 B1 (Askill et al.); etc. The methods and systems of the present invention may alternatively include an adhesive skin paint that includes pyroxylin-based adhesive compatible with wound care. One example of such a material is marketed under the tradename NEW-SKIN. The limited adhesion of the wound bridging portion that may be desired in connection with the present invention may be accomplished when using cyanoacrylate-based or pyroxylin-based adhesives by using, e.g., microporous polypropylene, polyester, etc. in contact with the wound edges. The cyanoacrylate-based adhesives described in U.S. Pat. No. 5,259,835 (Clark et al.) may be used in connection with the present invention if the materials of the wound closure are selected to limit adhesion of the wound closure to the skin using the flowable adhesive as discussed above.

Turning now to adhesive skin paints that are suitable for use with the present invention, it may be preferred that the adhesive skin paint used in connection with the present invention have a solvent system with an Alkane-Based Siloxy Polymer Reaction Solvent. An Alkane-Based Siloxy Polymer Reaction Solvent system typically contains primarily straight, branched or cyclic alkanes, and is capable of acting as the reaction solvent (i.e. the non-reactive fluid portion of a reaction composition) for the polymerization reaction of the specific monomer composition of TRIS (3-methacryloyloxypropyltris(trimethylsiloxy)silane)/Methyl Methacrylate/iso-octyl acrylate in a 53/39/8 weight ratio. The solvent system is readily identified in a routine evaluation by undertaking a polymerization reaction using the specific monomer composition described above under a Standard Polymerization Reaction as defined below.

A Standard Polymerization Reaction includes reacting 20% total monomer concentration by weight based on monomer plus solvent with VAZO 67 free radical initiator used at 0.3% by weight based on total monomer at a reaction temperature of 70° C. under nitrogen for 36 hours (or less time if greater than 90% monomer conversion has occurred). A solvent system is deemed to be an Alkane-Based Siloxy Polymer Reaction Solvent if, after cooling to room temperature, the reacted composition yields a clear, pourable solution of polymer, and the inherent viscosity ("IV" as tested by ASTM D2857-95 at 25° C. and according to principles discussed in "Experiments in Polymer Science," by Edward A. Collins, Jan Bares and Fred W. Billmeyer, New York, Wiley (1973) pp 146-153.) of the polymer product is measured in ethyl acetate solvent at a nominal solids concentration of 0.5% (w/v) is less than 0.5 dl/g. Solvents which yield polymer with inherent viscosity greater than 0.5 dl/g are unsuitable. A specific procedure for the test is detailed below.

A mixture of 4.24 g TRIS, 3.12 g methyl methacrylate and 0.64 g iso-octyl acrylate is dissolved in 32 g of solvent in a 4 oz narrow-mouth flint glass bottle and 0.024 g of VAZO 67 is added. The solution is purged with nitrogen at a flow rate of 1 liter/minute for two minutes to remove dissolved oxygen. The bottle is closed tightly with a teflon-lined metal cap and placed in a launder-o-meter preset at 70° C. for at least 24 hours. Conversion is determined from measurement of percent nonvolatile solids by loss on drying at 105° C. for 60 minutes.

Some preferred solvents for use with preferred adhesive skin paints of the present invention are selected from one or more C5-C12 straight, branched, or cyclic alkanes. Particularly preferred solvents may be methylcyclopentane; n-heptane; n-octane; n-nonane; 2,2,4-trimethyl pentane; 3,4-dimethyl hexane. The solvent system may also include a blend of solvents that are a mixture of straight, branched or cyclic C 1 O—C12 alkanes with one or more C5-Cq straight, branched or cyclic alkanes.

For example, some preferred solvent blends may include mixtures of one or more of n-decane, n-undecane or n-dodecane with one or more of methylcyclopentane; n-heptane; n-octane; n-nonane; 2,2,4-trimethyl pentane; 3,4-dimethyl hexane.

The liquid polymer-containing coating materials that may be used as adhesive skin paints in connection with this invention may include a siloxane containing polymer and a solvent system that is non-stinging to a user. Preferably the polymer is present from 1 to 40% by weight and the solvent is present in amounts of 60 to 99%. In connection with the present invention, the material preferably forms an adhesive connection between the edges of the wound in the space between adjacent pairs of wound closures or adjacent a single wound closure (when only one wound closure is used).

Patents, patent applications, and publications disclosed herein are hereby incorporated by reference (in their entirety) as if individually incorporated. It is to be understood that the above description is intended to be illustrative, and not restrictive. Various modifications and alterations of this invention will become apparent to those skilled in the art from the foregoing description without departing from the scope of this invention, and it should be understood that this invention is not to be unduly limited to the illustrative embodiments set forth herein.

The invention claimed is:

1. A wound closure system comprising:
   a quantity of a flowable adhesive skin paint comprising
   1-40% of a siloxane-containing polymer;
   60-99% of an Alkane-Based Siloxane Polymer Reaction Solvent; and
   0-15% of adjuvants; and
   at least one wound closure that comprises a backing, a wound bridging portion adapted to be placed over a wound, and a pressure sensitive adhesive, wherein the adhesive skin paint does not adhere the wound bridging portion of the at least one wound closure to skin.

2. A wound closure system comprising:
   a quantity of a flowable adhesive skin paint; and
   at least one wound closure that comprises a backing, a wound bridging portion adapted to be placed over a wound, and a pressure sensitive adhesive, wherein the adhesive skin paint does not adhere the wound bridging portion of the at least one wound closure to skin; and
   wherein the at least one wound closure comprises:
   opposing elastomeric end portions; and
   the wound bridging portion between the end portions;
   wherein the wound closure recovers at least 85% after being stretched 30%, and wherein the wound bridging portion stretches less than the end portions when subjected to the same force, whereby the wound bridging portion tends to maintain the wound closed against forces generated by stretching of skin.

3. A system according to any of claims 1-2, wherein adhesion strength between the wound bridging portion and skin is about 30 grams/centimeter or less.

4. A system according to any of claims 1-2, wherein the wound bridging portion is porous.

5. A system according to any of claims 1-2, wherein the wound bridging portion comprises microporous polypropylene film.

6. A system according to any of claims 1-2, wherein the adhesive skin paint comprises a cyanoacrylate-based adhesive.

7. A system according to any of claims 1-2, wherein the adhesive skin paint comprises a pyroxylin-based adhesive.

8. A system according to claim 1, wherein the at least one wound closure comprises:
   opposing elastomeric end portions; and
   a wound bridging portion between the end portions;
   wherein the wound closure recovers at least 85% after being stretched 30%, and wherein the wound bridging portion stretches less than the end portions when subjected to the same force, whereby the wound bridging portion tends to maintain the wound closed against forces generated by stretching of skin.

9. A system according to claim 8, wherein the wound bridging portion stretches 8% or less when the wound closure stretches 30%.

10. A system according to claim 8, wherein the wound bridging portion stretches 1% or less when the wound closure stretches 30%.

* * * * *

UNITED STATES PATENT AND TRADEMARK OFFICE
CERTIFICATE OF CORRECTION

PATENT NO. : 7,267,681 B2
APPLICATION NO. : 11/159010
DATED : September 11, 2007
INVENTOR(S) : Wayne K. Dunshee It is certified that error appears in the above-identified patent and that said Letters Patent is hereby corrected as shown below:

Column 1,
Line 7, delete "No" and insert in place thereof --No.--.

Column 2,
Line 39, delete "membranes" and insert in place thereof --membranes.--

Column 5,
Line 11, delete "DRAWING" and insert in place thereof --DRAWINGS--.

Column 9,
Line 43, delete "(which" and insert in place thereof --which--.

Column 10,
Lines 15-16, delete "(Greffet al.)" and insert in place thereof --(Greff et al.)--.
Line 62, delete "pp" and insert in place thereof --pp.-- and delete "153.)" and
  insert in place thereof --153)--.

Column 11,
Line 18, delete "C 1 O-C12" and insert in place thereof --C10-C12-- and delete
  "C5-Cq" and insert in place thereof --C5-C9--.

Signed and Sealed this

Third Day of June, 2008

JON W. DUDAS
*Director of the United States Patent and Trademark Office*